(12) United States Patent
André et al.

(10) Patent No.: US 12,311,155 B2
(45) Date of Patent: May 27, 2025

(54) ADMINISTRATION ASSEMBLY FOR A MEDICAMENT DELIVERY DEVICE AND A MEDICAMENT DELIVERY DEVICE COMPRISING THE SAME

(71) Applicant: SHL MEDICAL AG, Zug (CH)

(72) Inventors: Erika André, Saltsjö-Boo (SE); Linda Odelberg, Ekerö (SE); Anders Holmqvist, Värmdö (SE); Pär Leander, Nacka (SE)

(73) Assignee: SHL Medical AG, Zug (CH)

( * ) Notice: Subject to any disclaimer, the term of this patent is extended or adjusted under 35 U.S.C. 154(b) by 197 days.

(21) Appl. No.: 17/725,201

(22) Filed: Apr. 20, 2022

(65) Prior Publication Data
US 2022/0241518 A1   Aug. 4, 2022

Related U.S. Application Data

(63) Continuation of application No. 16/630,379, filed as application No. PCT/EP2018/067779 on Jul. 2, 2018, now Pat. No. 11,357,927.

(30) Foreign Application Priority Data

Jul. 12, 2017 (EP) ..................................... 17180913

(51) Int. Cl.
*A61M 5/32* (2006.01)
*A61M 5/20* (2006.01)
*A61M 5/315* (2006.01)

(52) U.S. Cl.
CPC .......... *A61M 5/326* (2013.01); *A61M 5/3158* (2013.01); *A61M 2005/208* (2013.01); *A61M 2005/3267* (2013.01)

(58) Field of Classification Search
CPC ............ A61M 5/326; A61M 2005/208; A61M 2005/3267; A61M 5/2033; A61M 2005/2073; A61M 5/3158
See application file for complete search history.

(56) References Cited

U.S. PATENT DOCUMENTS

2016/0008541 A1* 1/2016 Hirschel ................. A61M 5/24
 604/137
2018/0036491 A1* 2/2018 Maxfield ............. A61M 5/2033

FOREIGN PATENT DOCUMENTS

CH          707898 A2    10/2014
JP       2015-504713 A    2/2015
(Continued)

OTHER PUBLICATIONS

International Search Report and Written Opinion for Int. App. No. PCT/EP2018/067779, mailed Aug. 27, 2018.

*Primary Examiner* — Michael J Tsai
*Assistant Examiner* — Neeraja Gollamudi
(74) *Attorney, Agent, or Firm* — McDonnell Boehnen Hulbert & Berghoff LLP

(57) ABSTRACT

An administration assembly for a medicament delivery device is presented having a plunger rod, a plunger rod holder and an activation sleeve configured to receive a portion of the plunger rod holder. The triggering member is configured to move the activation sleeve from a first position to a second position relative to the plunger rod holder. The plunger rod is configured to be axially locked relative to the plunger rod holder when the activation sleeve is in the first position. The plunger rod is released from being axially locked when the activation sleeve is moved towards the second position.

20 Claims, 7 Drawing Sheets

(56) References Cited

FOREIGN PATENT DOCUMENTS

| | | |
|---|---|---|
| JP | 2016-512767 A | 5/2016 |
| TW | 201722493 A | 7/2017 |
| WO | 2011/043714 A1 | 4/2011 |
| WO | 2014/195183 A1 | 12/2014 |

* cited by examiner

ADMINISTRATION ASSEMBLY FOR A MEDICAMENT DELIVERY DEVICE AND A MEDICAMENT DELIVERY DEVICE COMPRISING THE SAME

CROSS REFERENCE TO RELATED APPLICATIONS

The present application is a continuation of U.S. patent application Ser. No. 16/630,379, filed Jan. 10, 2020, which is a U.S. National Phase application pursuant to 35 U.S.C. § 371 of International Application No. PCT/EP2018/067779 filed Jul. 2, 2018, which claims priority to European Patent Application No. 17180913.0 filed Jul. 12, 2017. The entire disclosure contents of these applications are herewith incorporated by reference into the present application.

TECHNICAL FIELD

The present disclosure generally relates to medical devices. In particular, it relates to an administration assembly for a medicament delivery device, and to a medicament delivery device comprising an administration assembly.

BACKGROUND

Medicament delivery devices, in particular automated administration devices such as auto-injectors, are typically spring-biased. A device of this type may be activated for example by pushing the device towards the injection site, whereby a delivery member cover is moved in the proximal direction further into the housing, causing the device activation, or by means of an external button or slider.

WO2011043714 discloses a medicament delivery device comprising a housing, a first activator member, a second activator member, a drive mechanism including a plunger rod and a first compression spring, and a needle shield sleeve. The second activator comprises proximally extending flexible tongues configured to engage with the plunger rod to retain the plunger rod in an axial position prior to activation. This engagement is obtained due to the first activator member, which circumferentially encloses the flexible tongues and delimits the radial movement by the flexible tongues. The flexible tongues are thus prevented from flexing radially outwards. The first activator member is configured to be moved in the distal direction inside the housing by the needle shield sleeve, away from the flexible tongues, allowing the flexible tongues to flex radially outwards to disengage from the plunger rod. The plunger rod is thereby able to travel in the proximal direction.

Prior to use, the flexible tongues are thus subjected to the forward-biasing force provided by the first compression spring, causing the flexible tongues to weaken over time. This mechanical weakening is obtained because the cross-sectional dimension of the flexible tongues is reduced over time since they are axially stretched by the spring force. Thus, if for example the medicament delivery device is kept in storage for a longer period of time, for example a couple of years, the plastic structure of the flexible tongues may be substantially weakened. The first compression spring will therefore have to be designed to provide a forward-biasing force which does not cause damage to the flexible tongues even after a long period of storage.

SUMMARY

There has been a trend towards liquid medicaments with higher viscosity. This trend has been driven due to medicaments which nowadays contain larger molecules than in the past. Such medicaments are typically biosimilars. To be able to expel medicaments with higher viscosity, a higher biasing force on the plunger rod is required. It would therefore be desirable to be able to provide a high plunger rod biasing.

In view of the above, a general object of the present disclosure is to provide an administration assembly for a medicament delivery device which solves or at least mitigates problems of the prior art.

There is hence according to a first aspect of the present disclosure provided an administration assembly for a medicament delivery device, comprising: a plunger rod, a first resilient member configured to bias the plunger rod in the proximal direction, an elongated plunger rod holder configured to receive the plunger rod, an activation sleeve configured to receive a portion of the plunger rod holder, and configured to move axially from a first position relative to the plunger rod holder to a second position, wherein the activation sleeve is configured to be biased towards the first position, wherein the plunger rod holder has a first hold and release structure and the plunger rod has a second hold and release structure, wherein in the first position the activation sleeve is configured to maintain the first hold and release structure in an axially locking contact position with the second hold and release structure in which the second hold and release structure is prevented from proximally directed movement relative to the first hold and release structure, thereby locking the plunger rod axially relative to the plunger rod holder, wherein in the second position the activation sleeve is configured to allow the first hold and release structure to move from the axially locking contact position, whereby biasing of the plunger rod provided by the first resilient member causes the second hold and release structure to act with a proximally directed force on the first hold and release structure, moving the first hold and release structure radially outwards from the axially locking contact position to thereby release the plunger rod from the plunger rod holder.

According to one embodiment the triggering member is a delivery member cover having a distal end configured to bear against a proximal end of the activation sleeve.

One embodiment comprises a second resilient member configured to bias the activation sleeve in the proximal direction towards the first position.

According to one embodiment the first hold and release structure includes a radially flexible first arm and a radially flexible second arm, the first arm and the second arm extending parallel with each other in the distal direction from their attachment to a main body of the plunger rod holder.

Thus, contrary to the prior art solution, the first arm will initially be in a compressed state. The first arm will thus not be subjected to a pulling force when the activation sleeve is in the first position, and consequently, there the first arm will not become mechanically weakened if stored for a longer period of time.

According to one embodiment the activation sleeve is configured to prevent radially outward flexing of the first arm and the second arm when the activation sleeve is in the first position, whereby the first hold and release structure is maintained in the axially locking contact position with the second hold and release structure.

According to one embodiment in the second position of the activation sleeve, the first arm and the second arm are allowed to be flexed or pivoted radially outwards.

According to one embodiment the first arm has a first radially inwards extending portion and the second arm has a second radially inwards extending portion.

According to one embodiment the first radially inwards extending portion and the second radially inwards extending portion are configured to extend towards each other, and are configured to be located proximally relative to the second hold and release structure when the activation sleeve is in the first position to block proximal movement of the second hold and release structure.

According to one embodiment the second hold and release structure comprises a radially outwards extending protrusion configured to bear against the first radially inwards extending portion and the second radially inward extending portion when the activation sleeve is in the first position.

According to one embodiment the second hold and release structure includes a first opening and a second opening, wherein the first radially inwards extending portion is configured to engage with the first opening and the second radially inwards extending portion is configured to engage with the second opening in the axially locking contact position of the first hold and release structure with the second hold and release structure, and wherein the first radially inwards extending portion is allowed to disengage from the first opening and the second radially inwards extending portion is allowed to disengage from the second opening when the activation sleeve is in the second position.

According to one embodiment the first radially inwards extending portion and the first opening have cooperating bevelled surfaces and the second radially inwards extending portion and the second opening have cooperating bevelled surfaces.

According to one embodiment the second hold and release structure includes a first radially outwards extending protrusion and a second radially outwards extending protrusion, wherein the first radially inwards extending portion is configured to bear against a first proximal face of the first radially outwards extending protrusion and the second radially inwards extending portion is configured to bear against a second proximal face of the second radially outwards extending portion in the axially locking contact position of the first hold and release structure, and wherein the first arm and the second arm are configured to flex radially outwards when the activation sleeve is moved to the second position thereby disengaging the first radially outwards extending protrusion and the second radially outwards extending protrusion from the first arm and the second arm.

According to one embodiment the first radially inwards extending portion and the first proximal face have cooperating bevelled surfaces, and the second radially inwards extending portion and the second proximal face have cooperating bevelled surfaces.

There is according to a second aspect of the present disclosure provided a medicament delivery device comprising: a housing, a triggering member configured to move the activation sleeve from the first position towards the second position, and an administration assembly according to the first aspect, configured to be received by the housing.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which:

FIG. 3b shows a perspective view of a plunger rod holder and a plunger rod of the administration assembly shown in FIG. 3a;

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component.

Similarly, the terms "transverse", "transversal" and "transversally" refer to a direction generally perpendicular to the longitudinal direction.

Figure 1:
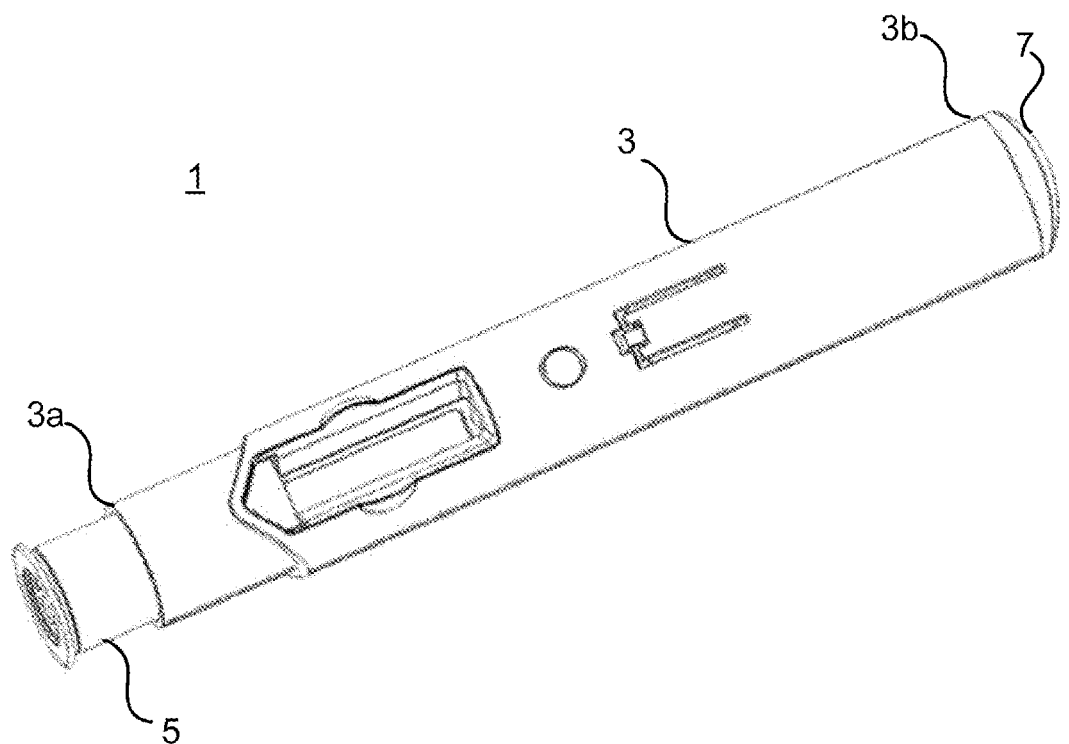
FIG. 1 is a perspective view of an example of a medicament delivery comprising an administration assembly.

FIG. 1 shows a perspective view of an example of a medicament delivery device 1. The exemplified medicament delivery device 1 is an auto-injector comprising an administration assembly, not shown, as will be described in more detail in what follows.

The medicament delivery device 1 comprises a housing 3 having a proximal end 3a and a distal end 3b, a delivery member cover 5 extending from a proximal opening in the proximal end 3a of the housing 3, and a rear end cap 7.

The delivery member cover 5 is biased in the proximal direction. The delivery member cover 5 is configured to be moved linearly, or axially, relative to the housing 3. The delivery member cover 5 is configured to be moved between an extended position relative to the housing 3, shown in FIG. 1, and a retracted position relative to the housing 3. In the retracted position, a greater portion of the delivery member cover 5 is received by the housing 3 than in the extended position. The delivery member cover 5 is configured to be biased towards the extended position.

Figure 2:
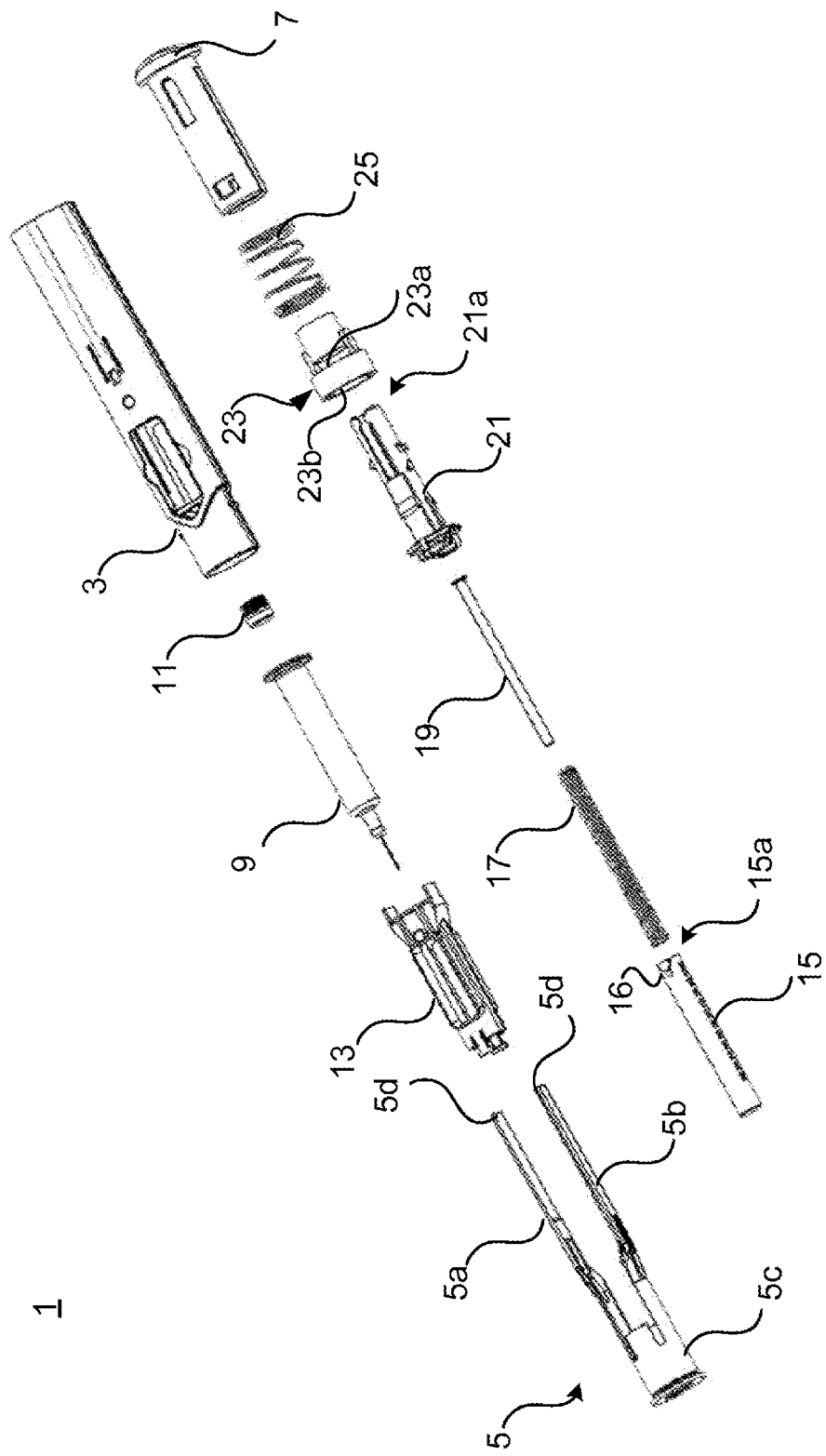
FIG. 2 shows an exploded view of the medicament delivery device in FIG. 1.

FIG. 2 shows an exploded view of the medicament delivery device 1. The delivery member cover 5 has a first delivery member cover arm 5a and a second delivery member cover arm 5b, and a cylindrical proximal portion 5c configured to extend from the housing 3 in the extended position of the delivery member cover 5. The first delivery member cover arm 5a and the second delivery member cover arm 5b extend in the distal direction from the proximal portion 5c.

In a fully mounted state, the medicament delivery device 1 may comprise a medicament container 9, a stopper 11 and a medicament container holder 13. The medicament container holder 13 is mounted in the housing 3 and configured to hold the medicament container 9. The medicament container 9 is configured to receive the stopper 11 through an open distal end thereof.

The medicament delivery device 1 further comprises an administration assembly 10 including a plunger rod 15, a first resilient member 17, for example a spring, a guide rod 19, a plunger rod holder 21, an activation sleeve 23 and a second resilient member 25, for example a spring. The administration assembly 10 also includes a triggering member, here exemplified by the delivery member cover 5.

The plunger rod holder 21 is configured to receive the plunger rod 15. The plunger rod has 15 has an inner axial channel, not shown. The first resilient member 17 is configured to be received by the plunger rod 15. In particular, the first resilient member 17 is configured to be received in the axial channel of the plunger rod 15. The first resilient member 17 is configured to receive the guide rod 19 when arranged in the axial channel. Bending of the highly stiff first resilient member 17 can thus be prevented.

The plunger rod 15 has a second hold and release structure 15a provided on a distal end portion of the outer surface of the plunger rod 15. In the present example, the second hold and release structure 15a includes a radially outwards extending protrusion, or wing 16.

The plunger rod holder 21 is configured to receive the plunger rod 15. Prior to use of the medicament delivery device 1, the plunger rod 15 is prevented from moving axially in the proximal direction relative to the plunger rod holder 21. Hereto, the plunger rod holder 21 has a first hold and release structure 21a configured to cooperate with the second hold and release structure 15a of the plunger rod 15. Prior to medicament administration, the first hold and release structure 21a is configured to be maintained by the activation sleeve 23 in an axially locking contact position with the second hold and release structure 15a.

The activation sleeve 23 is essentially cylindrical and configured to receive a portion of the plunger rod holder 21. The activation sleeve 23 is configured to be moved axially relative to the plunger rod holder 21 from a first or initial position to a second or release position located distally relative to the first or initial position. The activation sleeve 23 is configured to circumferentially enclose the plunger rod holder 21 and to cooperate with the first hold and release structure.

The activation sleeve 23 is configured to be moved by a triggering member, which in the present example is the delivery member cover 5, from the initial position to the release position. In particular, the delivery member cover 5 has a distal end 5d configured to bear against a proximal end 23b of the activation sleeve 23. In the present example, the first delivery member cover arm 5a and the second delivery member cover arm 5b are configured to bear against the proximal end 23b of the activation sleeve 23. When the activation sleeve 23 has been moved in the distal direction, to the second or release position, the first hold and release structure 21a is allowed to move from the axially locking contact position with the second hold and release structure 15a. The axially locking contact position of the first hold and release structure 21a with the second hold and release structure 15a is what maintains the plunger rod 15 in an axially interlocked state with the plunger rod holder 21. The plunger rod 15 will thus be allowed to move in the proximal direction, into the medicament container 9. A medicament contained therein may thereby be expelled.

The second resilient member 25 is configured to bias the activation sleeve 23 in the proximal direction. Due to this biasing, the activation sleeve 23 bears against the distal end 5d of the delivery member cover 5. According to the present example, the activation sleeve 23 has an outer surface provided with a distal flange 23a. The second resilient member 25 is configured to be mounted between the flange 23a and the rear end cap 7 so that it bears against the flange 23a and the rear end cap 7. The second resilient member 25 will thus bias the activation sleeve 23 in the proximal direction so that the proximal end 23b of the activation sleeve 23 contacts the distal end 5d of the delivery member cover 5.

Figure 3A:
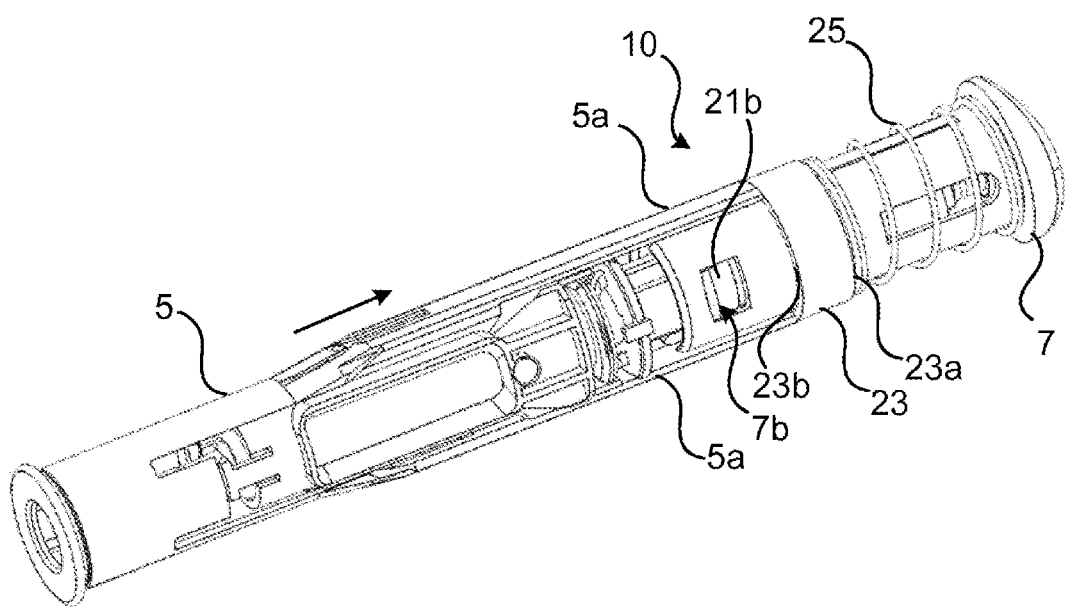
FIG. 3a shows a perspective view of a first example of an administration assembly of the medicament delivery device in FIG. 1.

Turning now to FIG. 3a, the medicament delivery device 1 is shown with the housing 3 removed. It can here be seen that the second resilient member 25 is provided between the rear end cap 7 and the flange 23a. By pushing the delivery member cover 5 in the distal direction as shown by the arrow, the activation sleeve 23 will move from the first position shown towards the second position thereof. The second resilient member 25 will thus become compressed and bias the activation sleeve 23 and the delivery member cover 5 in the proximal direction, i.e. towards their first position and extended position, respectively.

According to the present example, the rear end cap 7 has a tubular body 7a which is configured to receive a portion of the plunger rod holder 21. The tubular body 7a is configured to engage with the plunger rod holder 21. Hereto, the tubular body 7a has a recess 7b and the plunger rod holder 21 has a radial protrusion 21b configured to be received by the recess 7c. The rear end cap 7 and the plunger rod holder 21 thus become axially and rotationally locked relative to each other.

Figure 3B:
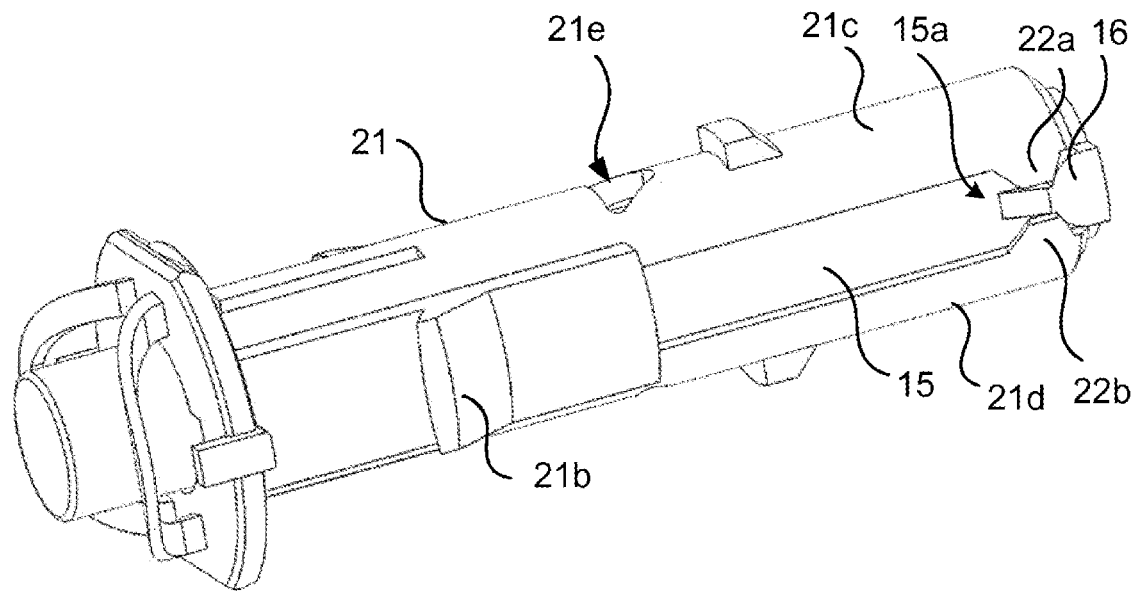

FIG. 3b shows the plunger rod holder 21 and the plunger rod 15 received therein. The plunger rod holder 21 has a radially flexible first arm 21c and a radially flexible second arm 21d. The first arm 21c and the second arm 21d form part of the first hold and release structure 21a. The first arm 21c and the second arm 21d extend parallel to each other from their attachment with the main body of the plunger rod holder 21. The first arm 21c and the second arm 21d extend in the distal direction from their attachment. The first arm 21c and the second arm 21d are hence distally extending arms. It should be noted that the first arm 21c and the second arm 21d may be integral with the main body of the plunger rod holder 21, as is the case in the present example.

According to the present example, the main body of the plunger rod holder 21 is provided with two radial through-openings 21e, of which only one is shown in FIG. 3b. The radial through-openings 21e weaken the mechanical strength of the plunger rod holder structure, and can be seen to form part of a respective hinge structure. The radial through-openings 21e hence facilitates for the first arm 21c and the second arm 21d to flex or pivot radially outwards.

The first arm 21c has a first radially inwards extending portion 22a. The second arm 21d has a second radially inwards extending portion 22b. The first radially inwards extending portion 22a and the second radially inwards extending portion 22b are axially aligned and provided at a distal end portion of the first arm 21c and the second arm 21d, respectively. The first radially inwards extending portion 22a and the second radially inwards extending portion 22b extend towards each other. The distance between the first arm 21c and the second arm 21d is hence shorter between the first radially inwards extending portion 22a and the second radially inwards extending portion 22b than elsewhere along the first arm 21c and the second arm 21d.

The plunger rod 15 is provided with the second hold and release structure 15a, which in the present example includes the radially outwards extending protrusion 16. The radially outwards extending protrusion 16 is provided on a distal end portion of the plunger rod 15. The first radially inwards extending portion 22a and the second radially inwards extending portion 22b are located proximally relative to the radially outwards extending protrusion 16 when the activation sleeve 23 is in the first position. The radially outwards extending protrusion 16 bears against the first radially inwards extending portion and the second radially inwards extending portion, as shown in FIG. 3b. In this case, the inner surface of the activation sleeve 23 bears against the first arm 21c and the second arm 21d, preventing the first arm 21c and the second arm 21d to flex or pivot radially outwards. On the other hand, when the activation sleeve 23 has been moved axially from the first position to the second position, the inner surface which previously prevented the first arm 21c and the second arm 21d to move radially outwards, has also been moved in the distal direction, distally past the first arm 21c and the second arm 21d. There is in this situation no longer a radially delimiting surface which prevents the first arm 21c and the second arm 21d to flex or pivot radially outwards. Due to the high proximal biasing provided by the first resilient member 17, the radially outwards extending protrusion 16 will urge the first arm 21c and the second arm 21d radially outwards. In this manner, the radially outwards extending protrusion will be able to move through the momentarily expanded gap between the first radially inwards extending portion 22a and the second radially inwards extending portion 22b.

Figure 4A:
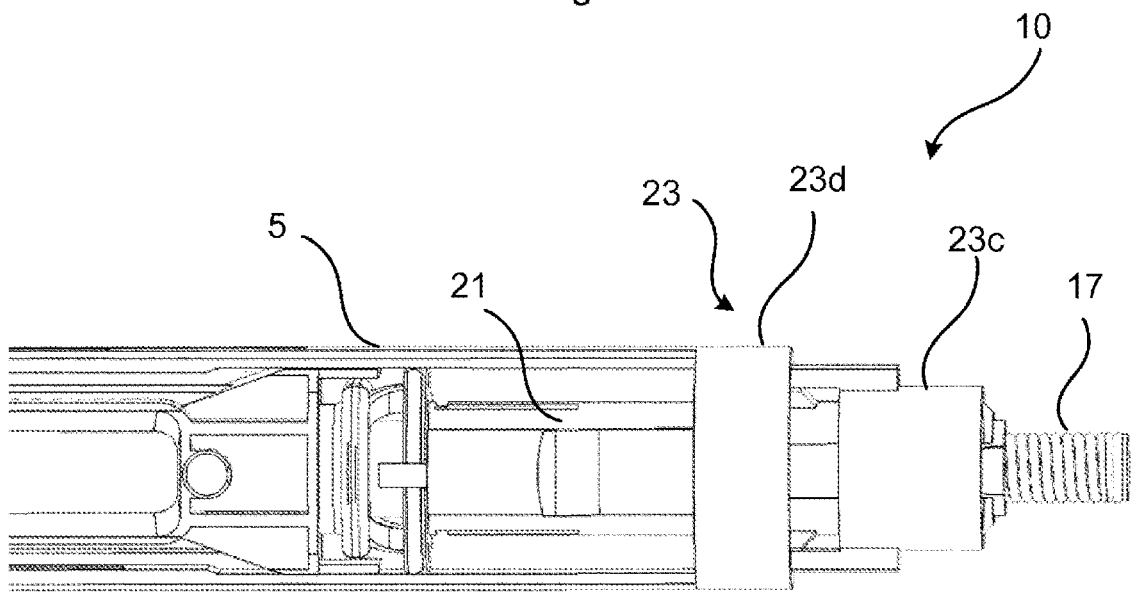
FIG. 4a shows a side view of the administration assembly.

FIG. 4a shows the administration assembly 10 with the activation sleeve 23 provided over the plunger rod holder 21. The activation sleeve 23 has a distal portion 23c and a proximal portion 23d. The distal portion 23c has a smaller inner diameter than the proximal portion 23d. In the first position of the activation sleeve 23, shown in FIG. 4a, the distal portion 23c circumferentially encloses the first arm 21c and the second arm 21d, thus preventing radial outward movement of the first arm 21c and the second arm 21d. When the activation sleeve 23 has been moved distally to the second position, the proximal portion 23d, which has a larger inner diameter than the distal portion 23c, will enclose the first arm 21c and the second arm 21d circumferentially.

Figure 4B:
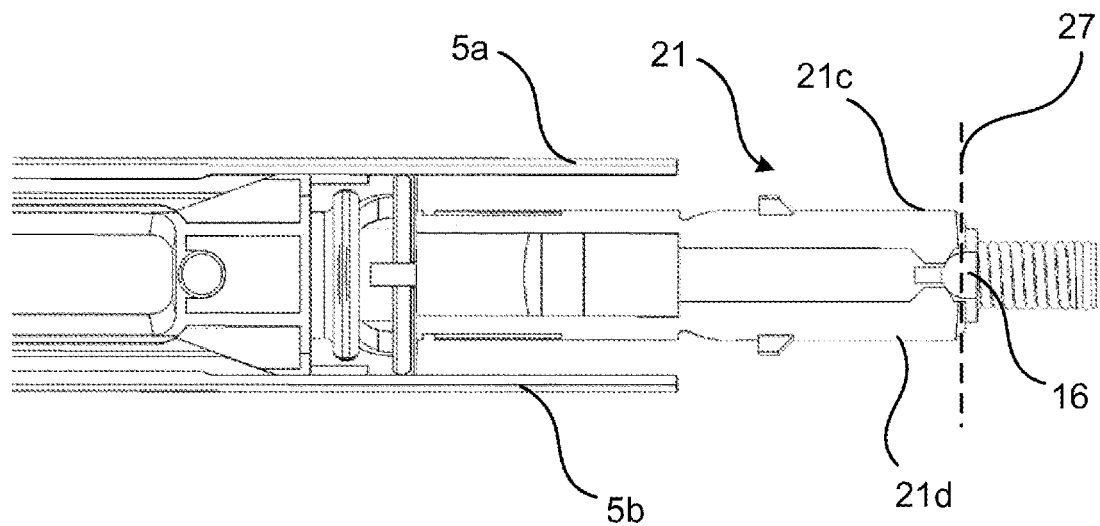
FIG. 4b shows a side view of the administration assembly.

In FIG. 4b, the activation sleeve 23 has been removed for the purpose of illustration of the components below. A line of activation 27 marks the axial position which the trailing edge of the distal portion 23d of the activation sleeve 23 has to cross when being moved distally, before the first arm 21c and the second arm 21d are allowed to move radially outwards.

Figure 5:
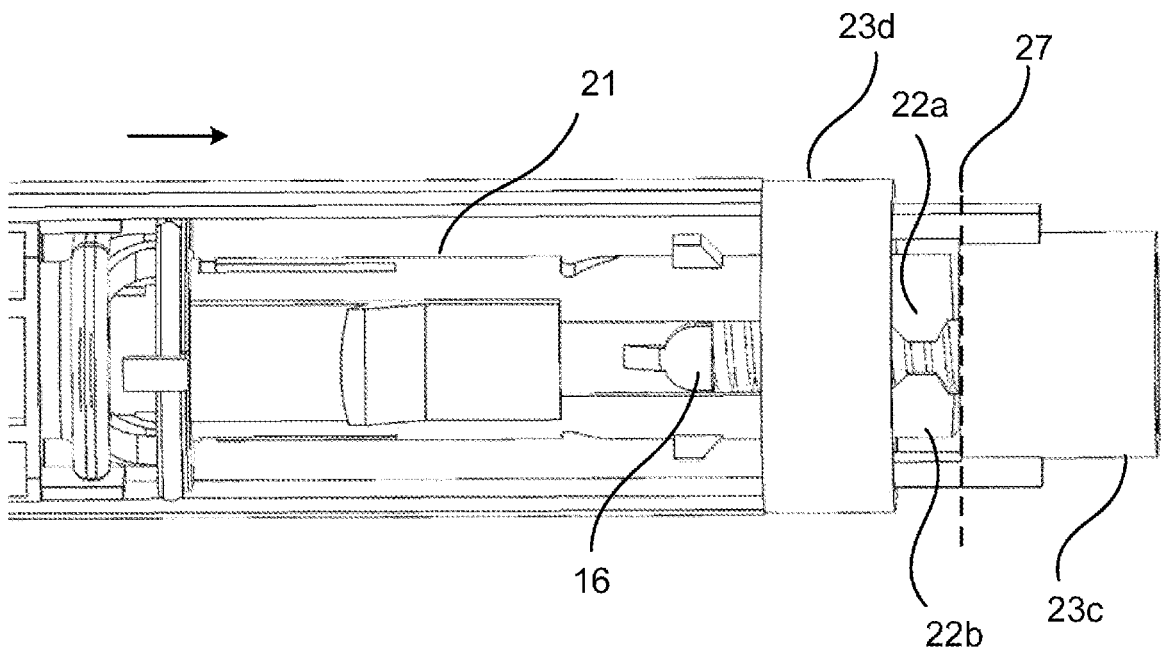
FIG. 5 show side a view of the administration assembly in FIGS. 4a and 4b with certain components removed.

In FIG. 5 a situation is shown in which the medicament delivery device 1 is in use, during medicament administration. Prior to medicament administration, the delivery member cover 5 is placed against the site of administration and pushed towards the site. As a result, the delivery member cover 5 is moved into the housing, from the extended position towards the retracted position. The delivery member cover 5 hence pushes the activation sleeve 23 in the distal direction, as shown by the arrow. In FIG. 5, the activation sleeve 23, in particular the distal portion 23c thereof, has moved past the line of activation 27. This results in that the second hold and release structure 15a, i.e. the radially outwards extending protrusion, pushes the first arm 21c and the second arm 21d radially outwards, allowing it to move past the first radially inwards extending portion 22a and the second radially inwards extending portion 22d. Once the second hold and release structure 15a has moved past the first radially inwards extending portion 22a and the second radially inwards extending portion 22b, the first arm 21c and the second arm 21c and the second arm 21d are moved back to their initial parallel positions shown in FIG. 5. The plunger rod 15 is now disengaged from the plunger rod holder 21, and can push the stopper 11 forward inside the medicament container, causing medicament expulsion.

Figure 6:
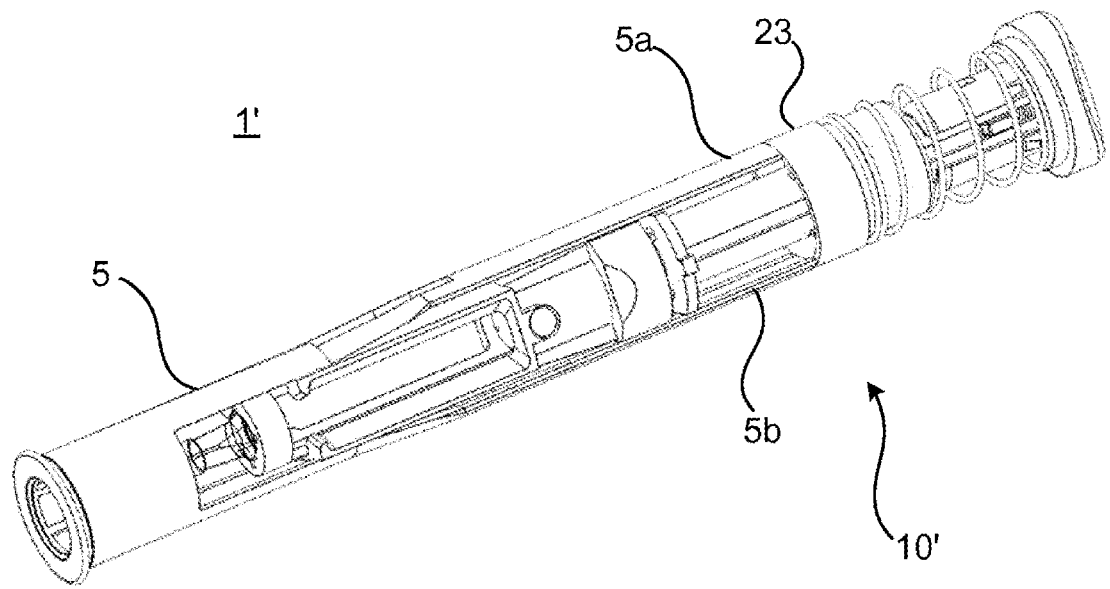
FIG. 6 is a perspective view of a second example of an administration assembly.

FIG. 6 show another example of a medicament delivery device 1' with its housing removed. This medicament delivery device 1' has an administration assembly 10' which differs from the previously described administration assembly 10. The plunger rod holder and the plunger rod constructions are different compared to the previous example.

Figure 7:
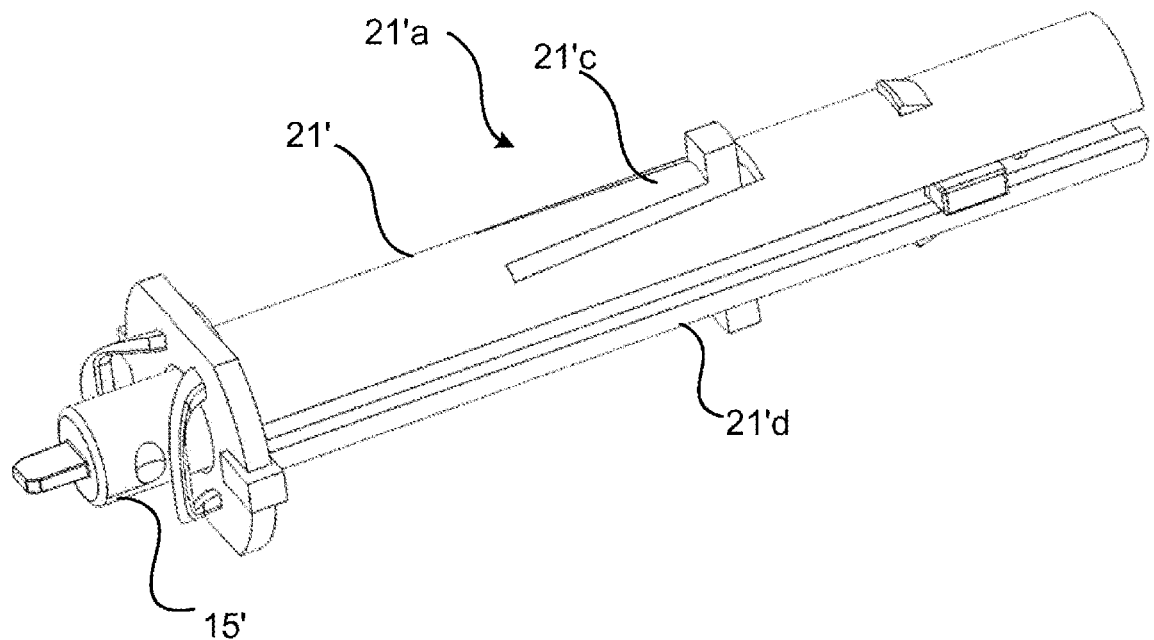
FIG. 7 depicts a perspective view of a plunger rod holder and a plunger rod of the administration assembly shown in FIG. 6.

FIG. 7 shows plunger rod holder 21' and plunger rod 15' received by the plunger rod holder 21'. Plunger rod holder 21' includes a radially flexible first arm 21'c and a radially flexible second arm 21'd. The first arm 21'c and the second arm 21'd form part of the first hold and release structure 21'a. The first arm 21'c and the second arm 21'd extend parallel to each other from their attachment with the main body of the plunger rod holder 21' in the distal direction. The first arm 21'*c* and the second arm 21'*d* are hence distally extending arms.

Figure 8A:
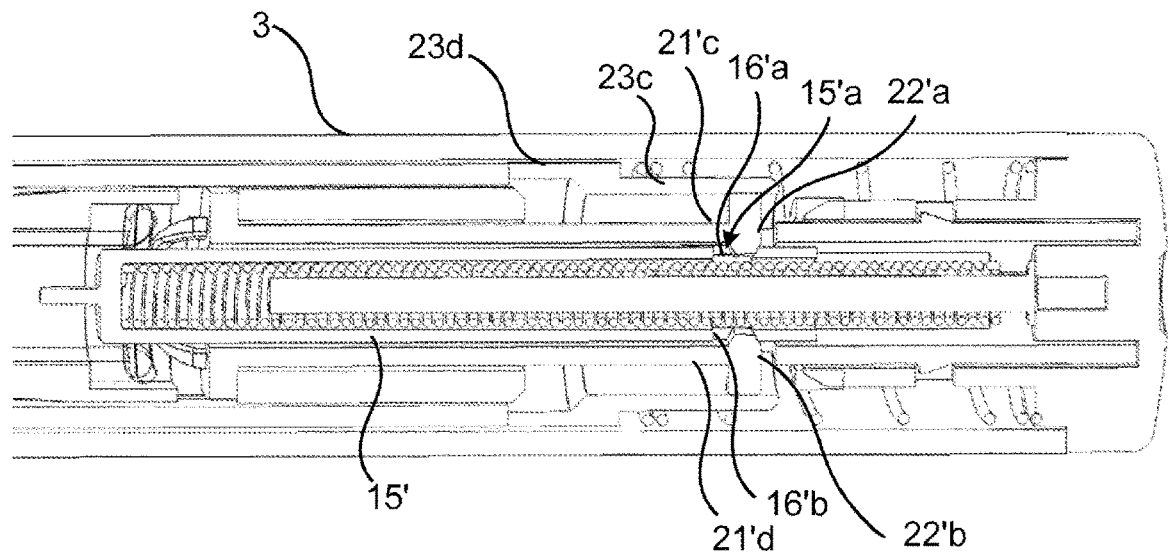
FIG. 8a shows a longitudinal section of a distal portion of a medicament delivery device containing the administration assembly shown in FIG. 6 in one state of operation.

FIG. 8*a* shows a longitudinal section of a distal portion of the medicament delivery device 1' in a default state, prior to medicament expulsion/administration.

According to the present example, the plunger rod 15' has a second hold and release structure 15'*a* including a first opening 16'*a* and a second opening 16'*b*. The first opening 16'*a* and the second opening 16'*b* are radial openings, provided in the outer surface of the plunger rod 15'. The first opening 16'*a* and the second opening 16'*b* are provided at about 180 degrees apart in the circumferential direction of the plunger rod 15'.

The first arm 21'*c* is provided with a first radially inwards extending protrusion 22'*a* and the second arm 21'*c* is provided with a second radially inwards extending protrusion 22'*b*. The first radially inwards extending protrusion 22'*a* is a first gripping member and is configured to engage with the first opening 16'*a* and the second radially inwards extending protrusion 22'*b* is a second gripping member configured to engage with the second opening 16'*b* when the activation sleeve 23 is in the first position, as shown in FIG. 8*a*.

The activation sleeve 23 has a distal portion 23*c* and a proximal portion 23*d*. The distal portion 23*c* has a smaller inner diameter than the proximal portion 23*d*. The first arm 21'*c* and the second arm 21'*d* bear against the inner surface of the distal portion 23*c* when the activation sleeve 23 is in the first position. The first arm 21'*c* and the second arm 21'*d* are hence in this situation prevented from flexing radially outwards. In the present example, the first arm 21'*c* has a protrusion which bears against the inner surface of the distal portion 23*c* and the second arm 21'*d* has a protrusion which bears against the inner surface of the distal portion 23*c* when the activation sleeve 23 is in the first position.

Figure 8B:
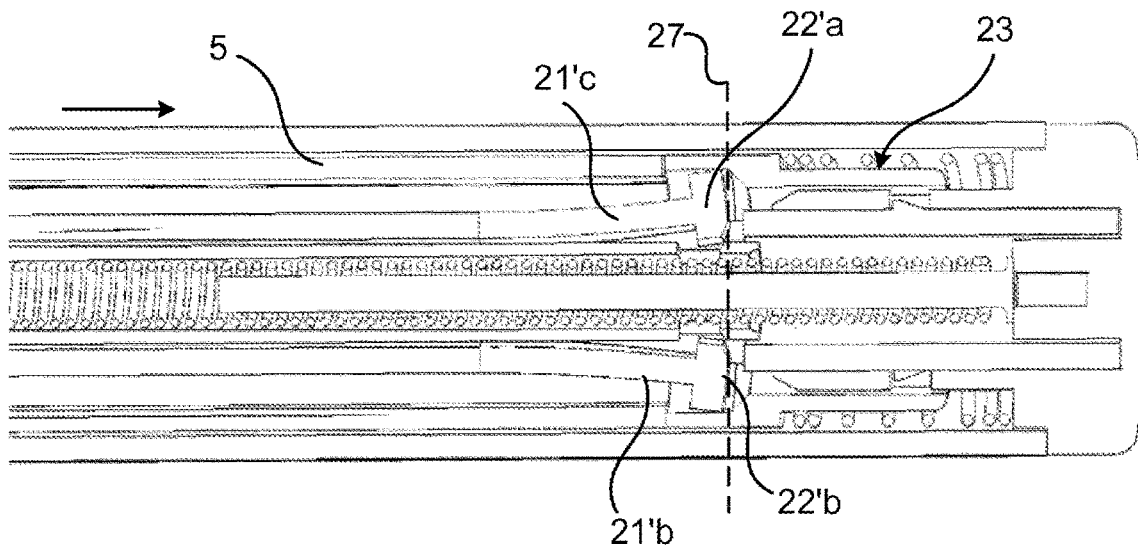
FIG. 8b shows a longitudinal section of a distal portion of a medicament delivery device containing the administration assembly shown in FIG. 6 in one state of operation.

FIG. 8*b* shows when medicament administration has commenced. The delivery member cover 5 has been moved from the extended position towards the retracted position and the activation sleeve 23 has been moved from the first position towards the second position. The activation sleeve 23 has just moved past the line of activation 27 and the first arm 21'*c* and the second arm 21'*d* have thus been allowed to flex radially outwards, as shown. The first radially inwards extending portion 22'*a* and the second radially inwards extending portion 22'*b* hence disengage from the first opening 16'*a* and the second opening 16'*b* of the plunger rod 15', allowing the plunger rod 15' to move in the proximal direction.

The first opening 16'*a* and the first radially inwards extending portion 22'*a* may have cooperating bevelled surfaces. The second opening 16'*b* and the second radially inwards extending portion 22'*b* may have cooperating bevelled surfaces. These cooperating bevelled surfaces facilitate disengagement between the plunger rod holder 21' and the plunger rod 15'.

Figure 8C:
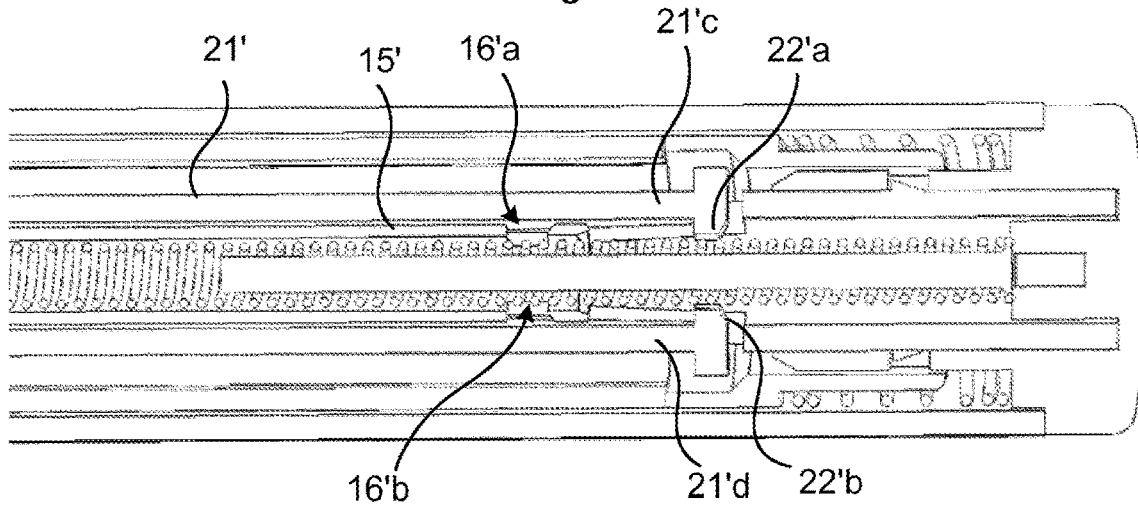
FIG. 8c shows a longitudinal section of a distal portion of a medicament delivery device containing the administration assembly shown in FIG. 6 in one state of operation.

In FIG. 8*c*, the plunger rod 15' has been released from its engagement with the plunger rod holder 21' and moved in the proximal direction relative to the plunger rod holder 21'. The first arm 21'*c* and the second arm 21'*d* have been moved back radially inwards to their initial position.

Figure 9A:
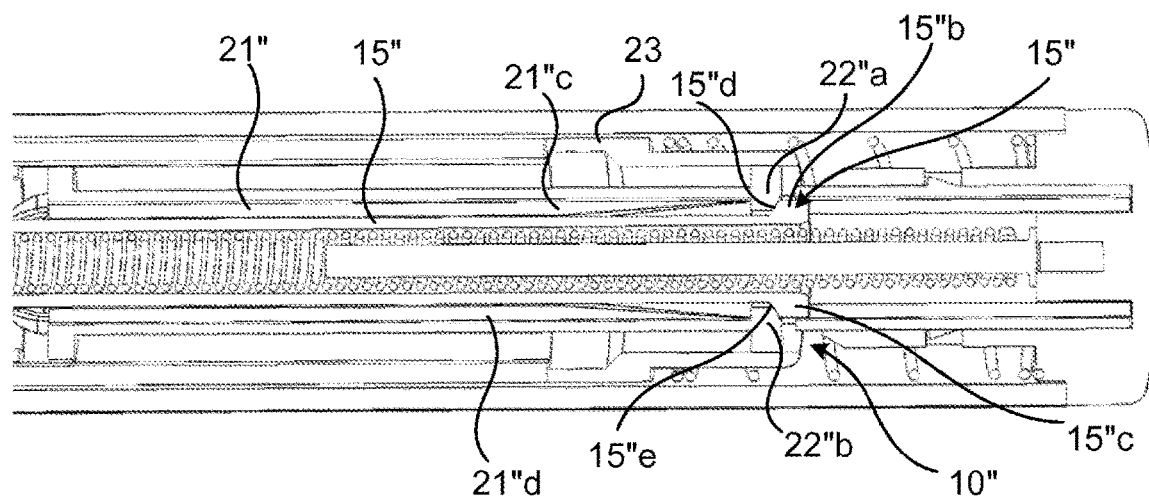
FIG. 9a shows a longitudinal section of a distal portion of a medicament delivery device containing a variation of the administration assembly shown in FIG. 6 in one state of operation.
Figure 9B:
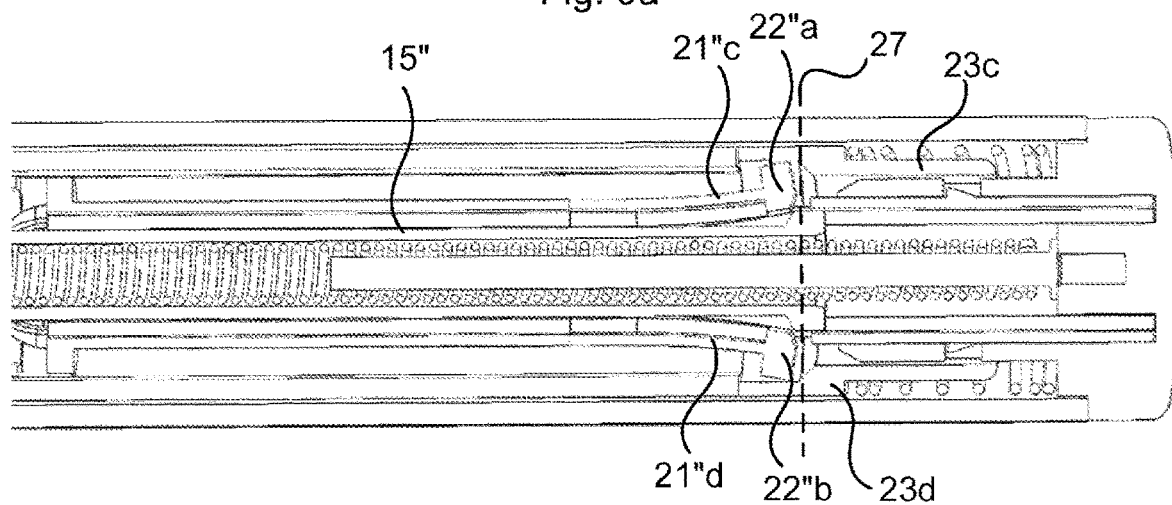
FIG. 9b shows a longitudinal section of a distal portion of a medicament delivery device containing a variation of the administration assembly shown in FIG. 6 in one state of operation.
Figure 9C:
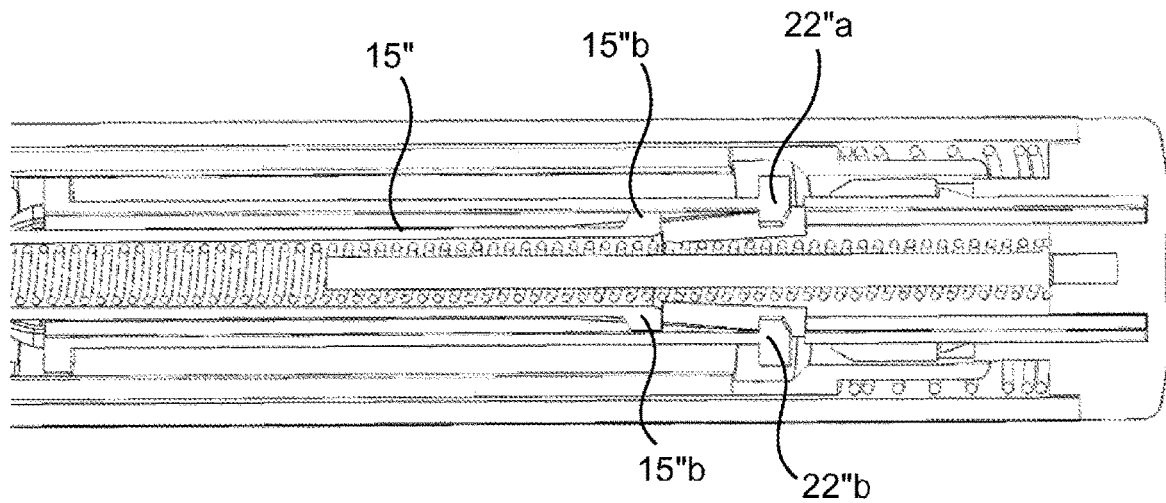
FIG. 9c shows a longitudinal section of a distal portion of a medicament delivery device containing a variation of the administration assembly shown in FIG. 6 in one state of operation.

FIGS. 9*a*-9*c* show a variation of the plunger rod 15' and the plunger rod holder 21'. In this example plunger rod 15" has a second hold and release structure 15" including a first radially outwards extending protrusion 15"*b* and a second radially outwards extending protrusion 15"*c*. The first radially outwards extending protrusion 15"*b* and the second radially outwards extending protrusion 15"*c* are arranged at a distal end portion of the plunger rod 15". The plunger rod holder 21" is similar to the example in FIGS. 8*a*-8*c* but here the inner surface of the first arm 21"*c* is inclined, with the radial thickness of the first arm 21"*c* increasing in the proximal direction. Moreover, the inner surface of the second arm 21"*d* is inclined, with the radial thickness of the second arm 21"*d* increasing in the proximal direction. This configuration facilitates radial outwards flexing/bending of the first arm 21"*c* and the second arm 21"*d*.

The first radially outwards extending protrusion 15"*b* has a first proximal face 15"*d* configured to bear against the first radially inwards extending portion 22"*a*. The second radially outwards extending protrusion 15"*c* has a second proximal face 15"*e* configured to bear against the second radially inwards extending portion 22"*b*. The first proximal face 15"*d* is bevelled as is the corresponding surface of the first radially inwards extending portion 22"*a*. The second proximal face 15"*e* is bevelled as is the corresponding surface of the second radially inwards extending portion 22"*b*. This configuration facilitates radial expansion of the first arm 21"*c* and the second arm 21"*d* when the distal portion of the activation sleeve 23 moves past the line of activation 27 shown in FIG. 9*b*.

In FIG. 9*b* the distal portion 23*c* of the activation sleeve 23 has moved past the line of activation 27. The first arm 21"*c* and the second arm 21"*d* will hence be flexed radially outwards, allowing the proximally biased plunger rod 15", and in particular the first radially outwards extending portion 15"*b* and the second radially outwards extending portion 15"*c*, to pass under the first radially inwards extending portion 22"*a* and the second radially inwards extending portion 22"*b*.

FIG. 9*c* shows when the first radially outwards extending protrusion 15"*b* and the second radially outwards extending protrusion 15"*c* have moved past the first radially inwards extending portion 22"*a* and the second radially inwards extending portion 22"*b* and the plunger rod 15" has moved in the proximal direction.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. An activation mechanism for a medicament delivery device, comprising:
   a housing;
   a plunger rod having a first axial position, where activation of the medicament delivery device causes the plunger rod to move relative to the housing from the first axial positon to a second axial position;
   a first resilient member that is operatively engaged with the plunger rod to exert a biasing force on the plunger rod in a proximal direction;
   an end cap rotationally and axially fixed to the housing throughout a duration of the activation of the medicament delivery device;
   a plunger rod holder comprising a first hold and release structure that is releasably engaged with a second hold and release structure on the plunger rod when the plunger rod is in the first axial positon, where the biased plunger rod exerts a radial biasing force on the first hold and release structure, and wherein the plunger rod holder is rotationally and axially fixed to the end cap throughout the duration of the activation of the medicament delivery device;

an activation sleeve slidably positioned relative to and partially surrounding the first hold and release structure, where axial movement of the activation sleeve from a first position to a second position causes disengagement of the first hold and release structure from the second hold and release structure, wherein the activation sleeve when in the first position maintains the engagement of first hold and release structure with the second hold and release structure to lock the plunger rod axially relative to the plunger rod holder, and wherein the disengagement of the first hold and release structure from the second hold and release structure is caused by the proximal biasing of the plunger rod which causes the second hold and release structure to act with a proximally directed force on the first hold and release structure such that the first hold and release structure moves radially outwards to unlock the plunger rod from the first axial position so that it can move to the second axial position.

2. The activation mechanism as claimed in claim 1, wherein the first hold and release structure includes a radially flexible arm that extends in a distal direction from a main body of the plunger rod holder.

3. The activation mechanism as claimed in claim 2, wherein the activation sleeve has an inside surface that prevents radially outward flexing of the radially flexible arm when the activation sleeve is in the first position such that the first hold and release structure remains in engagement with the second hold and release structure.

4. The activation mechanism as claimed in claim 2, wherein when the activation sleeve is in the second position, the radially flexible arm will be flexed or pivoted radially outwards as a result of the biasing force exerted on the plunger rod by the resilient member.

5. The activation mechanism as claimed in claim 2, wherein the radially flexible arm has a radially inwards extending portion.

6. The activation mechanism as claimed in claim 5, wherein the radially inwards extending portion will be located proximally relative to the second hold and release structure when the activation sleeve is in the first position to block proximal movement of the second hold and release structure.

7. The activation mechanism as claimed in claim 5, wherein the second hold and release structure comprises a radially outwards extending surface that abuts the radially inwards extending portion when the activation sleeve is in the first position.

8. The activation mechanism as claimed in claim 7, wherein the radially inwards extending portion and the radially outwards extending surface both have cooperating beveled surfaces.

9. The activation mechanism as claimed in claim 1, wherein the first hold and release structure comprises two radially flexible arms that extend in a distal direction from a main body of the plunger rod holder.

10. The activation mechanism as claimed in claim 1, wherein the second hold and release structure includes a first radially outwards extending surface and a second radially outwards extending surface, where the first hold and release structure comprises a first arm having a first radially inwards extending portion and a second arm having a second radially inwards extending portion, where the first radially inwards extending portion abuts against a first proximal face of the first radially outwards extending surface and the second radially inwards extending portion abuts against a second proximal face of the second radially outwards extending surface when the activation sleeve is in the first position, and where the first arm and the second arm flex radially outwards when the activation sleeve is moved to the second position causing disengagement of the first radially outwards extending surface and the second radially outwards extending surface from the first arm and the second arm.

11. The activation mechanism as claimed in claim 10, wherein the first radially inwards extending portion and the first proximal face have cooperating beveled surfaces, and the second radially inwards extending portion and the second proximal face have cooperating beveled surfaces.

12. The activation mechanism as claimed in claim 1, wherein the activation sleeve has a first inside diameter and a second inside diameter.

13. The activation mechanism as claimed in claim 12, wherein the first inside diameter is smaller than the second inside diameter and abuts the first hold and release structure when the activation sleeve is in the first position.

14. The activation mechanism as claimed in claim 1 further comprising a delivery member cover configured to move the activation sleeve from the first position towards the second position.

15. The activation mechanism as claimed in claim 14, wherein the delivery member cover has a distal end configured to bear against a proximal end of the activation sleeve when the delivery member cover is retracted into the housing.

16. The activation mechanism as claimed in claim 14, wherein the delivery member cover is biased in a proximal directed by a second resilient member.

17. A medicament delivery device comprising:
a delivery member cover configured to move the activation sleeve from the first position towards the second position, and
an activation mechanism as claimed in claim 1.

18. The medicament delivery device according to claim 17, wherein the delivery member cover has a distal end configured to bear against a proximal end of the activation sleeve when the delivery member cover is retracted into the housing.

19. The medicament delivery device of claim 17, wherein the first hold and release structure further comprises:
a radially flexible first arm; and
a radially flexible second arm,
wherein the first arm and the second arm extend parallel with each other in the distal direction from their attachment to a main body of the plunger rod holder,
wherein when the activation sleeve is in a first position, the first arm and the second arm cannot flex radially outward, and
wherein when the activation sleeve is in the second position, the first arm and the second arm will flex or pivot radially outwards relative to the plunger rod.

20. The medicament delivery device of claim 17, wherein the activation sleeve has a first inside diameter and a second inside diameter, where the first inside diameter is smaller than the second inside diameter and abuts the first hold and release structure when the activation sleeve is in the first position, and
wherein when the delivery member cover moves distally, the activation sleeve moves distally relative to the first hold and release structure such that the second inside diameter is adjacent to the first hold and release structure.

\* \* \* \* \*